United States Patent [19]

Zisapel

[11] Patent Number: 5,498,423
[45] Date of Patent: Mar. 12, 1996

[54] METHOD FOR CORRECTING PLASMA MELATONIN LEVELS AND PHARMACEUTICAL FORMULATION COMPRISING MELATONIN

[75] Inventor: Nava Zisapel, Tel Aviv, Israel

[73] Assignee: Neurim Pharmaceuticals (1991) Ltd., Israel

[21] Appl. No.: 195,577

[22] Filed: Feb. 14, 1994

Related U.S. Application Data

[63] Continuation of Ser. No. 697,714, May 9, 1991, abandoned.
[51] Int. Cl.$^6$ ................................................ A61K 9/20
[52] U.S. Cl. .................... 424/464; 424/462; 424/482; 424/497; 424/489
[58] Field of Search .................... 424/464, 482, 424/497, 462

[56] References Cited

U.S. PATENT DOCUMENTS

| | | | |
|---|---|---|---|
| 4,600,723 | 7/1986 | Short et al. | 514/416 |
| 4,654,361 | 3/1987 | Samples et al. | 514/419 |
| 4,800,087 | 1/1989 | Mehta | 424/497 |
| 4,855,325 | 8/1989 | Naftchi | 514/634 |
| 4,882,137 | 11/1989 | Staples | 424/423 |
| 4,945,103 | 7/1990 | Cohen | 514/419 |

FOREIGN PATENT DOCUMENTS

| | | |
|---|---|---|
| 012630 | 11/1984 | European Pat. Off. . |
| 0246910 | 11/1987 | European Pat. Off. . |
| 0330652 | 8/1989 | European Pat. Off. . |
| 043856 | 7/1991 | European Pat. Off. . |
| 8503227 | 8/1985 | WIPO . |
| 8807370 | 10/1988 | WIPO . |
| 8904659 | 6/1989 | WIPO .................... 424/83 |

OTHER PUBLICATIONS

Aldhous et al., Br. J. Clin. Pharmac. 19, 517–521 (1985).
Arendt, Josephine and Broadway James (1987); Light and melatonin as zeitgebers in man. Chronobiology International 4:277–282.
James, Steven P., Sack, David A., Rosenthal, Norman E., and Mendelson, Wallace B. (1990); Melatonin administration in insomnia. Neuropsychopharmacology 3:19–23.
James, Steven P., Mendelson, Wallace B., Sack, David A., Rosenthal, Norman E. and Wehr, Thomas A., (1987); The effect of melatonin on normal sleep. Neuropsychopharmacology 1:41–44.
Sturner et al.: "Melatonin concentrations in the sudden infant death syndrome", & Forensic Sci. Int. (ireland), 1990, 45/1–2 (171–180).
Wurtman et al.: "Melatonin in Humans: Possible Involvement in SIDS. and use in Contraceptives", & Adv. Pineal Res. 1991, 5, 319–27.
James et al., "Neuropsychopharmacology", vol. 3, No. 1 pp. 19–23 (1990).
James et al., "Neuropsychopharmacology", vol. 1, No. 1 pp. 41–44 (1987).
Dahlitz et al., The Lancet, 337, 1121–1124, 1991.
Laudon et al., Neuroendocrinology, 48,577, 1988.

*Primary Examiner*—Thurman K. Page
*Assistant Examiner*—William E. Benston, Jr.
*Attorney, Agent, or Firm*—Rothwell, Figg, Ernst & Kurz

[57] ABSTRACT

In order to correct a melatonin deficiency or distortion in the plasma melatonin level and profile in a human subject, there is administered to a human in which such a deficiency or distortion had been diagnosed, over a predetermined time period including at least part of the nocturnal period, an amount of melatonin in controlled-release form, such that the melatonin is released according to a profile which, taking into account the existing profile, simulates the profile in plasma of a human having a normal endogenous melatonin plasma profile. The invention also relates to a pharmaceutical controlled-release formulation, which comprises melatonin in combination with at least one pharmaceutical carrier, diluent or coating, the formulation being adapted to release melatonin over a predetermined time period, according to a profile which, taking into account the existing profile, simulates the profile in plasma of a human having a normal endogenous melatonin profile. The method of the invention may be e.g. applied to the prevention of sudden infant death syndrome in infants, and then comprises a preliminary screening step in order to determine the plasma melatonin levels, in order to select infants having a deficient plasma melatonin level.

10 Claims, 1 Drawing Sheet

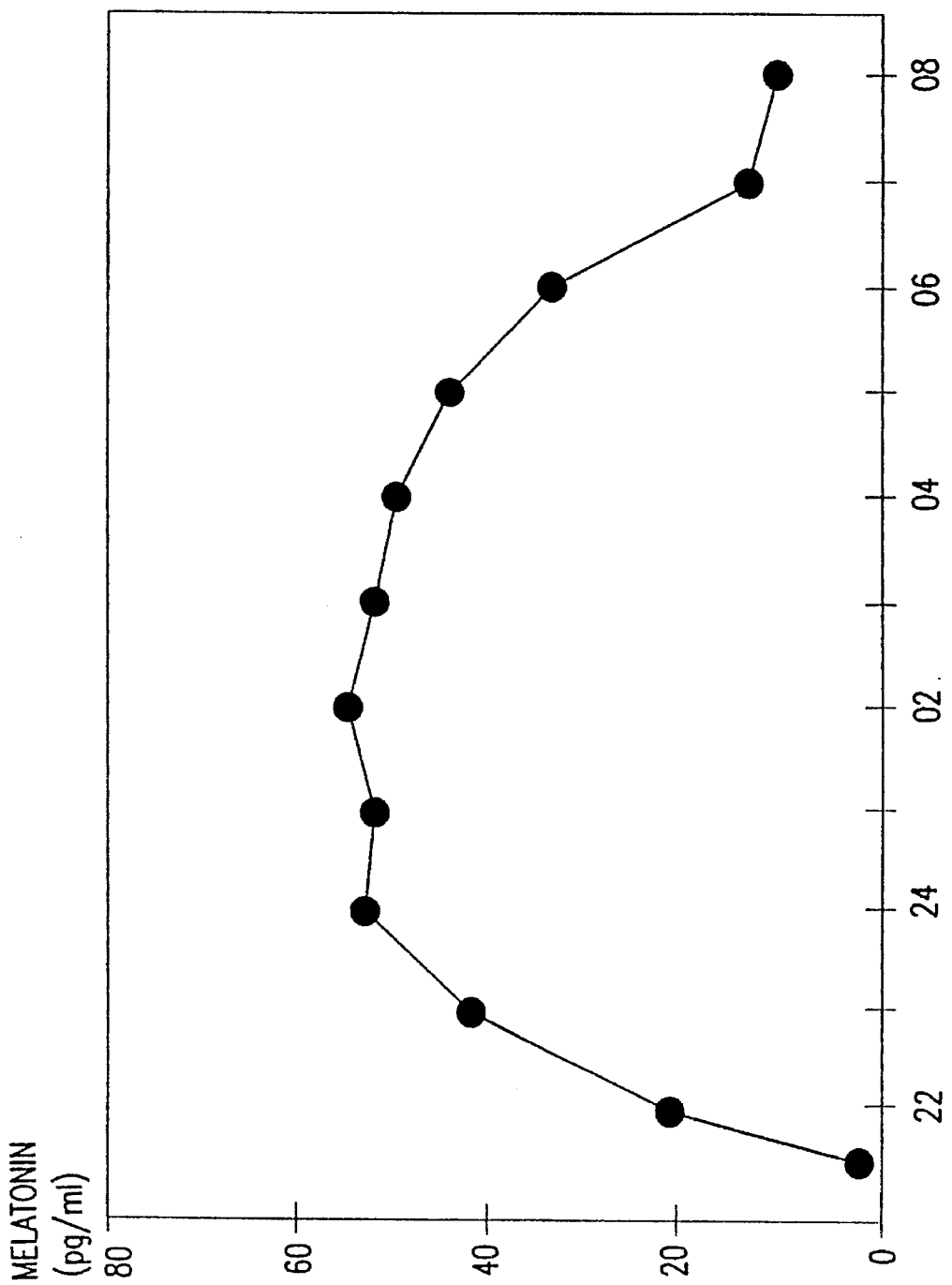

METHOD FOR CORRECTING PLASMA MELATONIN LEVELS AND PHARMACEUTICAL FORMULATION COMPRISING MELATONIN

This application is a continuation of application Ser. No. 07/697,714, filed May 9, 1991, now abandoned.

FIELD AND BACKGROUND OF THE INVENTION

The present invention relates to a method for correcting a deficiency or distortion in the plasma melatonin level and profile in a human subject and to a pharmaceutical controlled-release formulation which comprises melatonin.

Melatonin is the principal hormone secreted by the pineal gland in all vertebrates. In all mammals studied to date, including humans, a nocturnal rise in the production of melatonin by the pineal gland is evident, regardless of whether the mammals are nocturnal or diurnal, and conversely, melatonin production by the body is acutely suppressed by light. Melatonin is involved in the coordination of photoperiod and physiological processes, e.g. in animals which use changes in the photoperiod to time their thermoregulation, temporal signals to the thermoregulatory system are controlled by the daily rhythm in the duration of melatonin during the dark phase. Numerous studies have shown that melatonin has a potent influence on gonadal activity.

The timing of melatonin administration has been shown to be crucial for its biological activities. E.g., while in the case of rats whose circadian rhythms are disrupted or arrhythmic in constant light, as well as in the case of rats free running in constant darkness, their rhythms are synchronized by daily melatonin injections, by contrast it has been found that continuous availability of melatonin in circulation, of injection of melatonin in the morning, sometimes prevents gonodal responses to melatonin in the afternoon. The inventor has shown, e.g. in Zisapel et al, Neuroendocrinology 40: 102 (1985), that the inhibition by melatonin of the stimulated release of dopamine from rat hypothalamus, was highest in the early photophase and lowest in the early afternoon.

The ability of the animals or humans to respond to the melatonin signal may depend upon melatonin receptors. Thus, it has been shown that in Syrian hamsters, under a daily schedule of 14 hours light/10 hours darkness, the densities of melatonin binding sites in discrete brain areas (hypothalamus, medulla-pons and hippocampus) vary significantly over the 24-hour period with different patterns and phases, but no such variation was observed in other brain areas (striatum, parietal cortex, cerebellum). Only a partial overlap existed between the timing of peaks or troughs of melatonin binding sites and crests or nadirs in tissue melatonin content, so that the rhythms in melatonin binding sites may not be due to autoregulation of the receptors by the endogenous hormone. In this connection, it has also been shown that injection of exogenous melatonin to young rats or hamsters in the morning or late afternoon did not affect the density or diurnal variations in melatonin binding sites in most brain areas; in the hippocampus and midbrain, melatonin injected in the morning prevented the usual late afternoon rise in melatonin binding sites, whereas melatonin injected in the late afternoon suppressed the nocturnal rise in melatonin binding sites in the midbrain only.

It is also known that exogenously administered melatonin when administered in the late afternoon elicits antigonadal responses and decreases serum concentrations of testosterone in hamsters and immature rats, whereas in pinealectomized hamsters held in long days, the duration of melatonin administration is crucial in that 10 h infusions long days elicit gonadal regression in hamsters while after previous exposures to short days, 4–6 hour infusions of melatonin stimulated the gonads.

It is further known that in several species, including rats and humans, night-time melatonin production in the pineal gland declines with age. Moreover, a decline in 24 hour mean values and loss of circadian variations in melatonin binding sites was found to occur in discrete areas of the aged rat brain, as indicated by use of $^{125}$I-melatonin as a probe (Laudon et al, Neuroendocrinology, 48: 577, 1988). While the melatonin rhythm might not be the cause for the $^{125}$I-melatonin binding rhythms recorded in the rat brain, the possibility exists that the decline in amplitude of the melatonin rhythm leads to the dispersal of phase, resulting in the obliteration of rhythmicity in melatonin binding sites in the brain. In other words, the age-related decrease in melatonin levels and binding site density may lead to a decline in the ability of the neupoendocrine system to respond to photoperiodic messages.

U.S. Pat. No. 4,600,723 discloses the administration of melatonin in order to alleviate of prevent the negative effects of disturbances in circadian rhythms of bodily performance and function, such as may occur in a change of work patterns from day to night shift, or in cases of jet lag. Although conventional oral administration is exemplified, there is mentioned the possibility of administering melatonin a slow release form to maintain high plasma levels for the whole sleep period.

U.S. Pat. No. 4,654,361 discloses the administration of melatonin order to lower intraocular pressure in a human, where such pressure is abnormally high. Conventional oral and topical routes of administration are mentioned.

U.S. Pat. No. 4,945,103 discloses a method of treating premenstrual syndrome by administering melatonin at dosage levels sufficient to alleviate the symptoms. The melatonin may be administered orally or parenterally, or in the form of an implant or suppository which will provide a sustained release of melatonin Over time.

PCT Patent Application No. W0 88/07370 discloses the administration of melatonin for the purpose of inhibiting ovulation in human females, thereby effecting contraception, as well as for preventing breast cancer in women. The melatonin may be administered orally or parenterally, or in the form of an implant providing a sustained release of melatonin over time.

PCT Patent Application No. W0 89/04659 discloses the use of melatonin or related compounds, as a component in pharmaceutical compositions in order to counteract the effects of aging.

European Patent Application No. 0330625A2 discloses the production of melatonin and analogs thereof, as well as the use of melatonin administered orally. intramuscularly or endovenously for various therapeutic purposes. Also disclosed is the administration of melatonin in combination with an azidothymidine for the treatment of AIDS.

The entire contents of U.S. Pat. No. 4,600,723, U.S. Pat. No. 4,654,361, U.S. Pat. No. 4,945,103, PCT Patent Application No. W0 88/07370, PCT Patent Application No. WO 89/04659 and European Patent Application No. 0330625A2 are explicitly incorporated herein by reference.

Neither the scientific literature on the subject of melatonin, nor any of the above-mentioned Patents or published Patent Applications disclose or suggest the possibility or the desirability of either formulating or administering melatonin, so that it is released in the human body in a melatonin-deficient subject, in simulation of the profile in plasma of a human having a normal endogenous melatonin plasma profile.

SUMMARY OF THE INVENTION

The present invention provides in one aspect a method for correcting a melatonin deficiency or distortion in the plasma melatonin level and profile in a human subject, which comprises administering to a human in which such a deficiency or distortion had been diagnosed, over a predetermined time period including at least part of the nocturnal period, an amount of melatonin in controlled-release form, such that the melatonin is released according to a profile which, taking into account the existing profile, simulates the profile in plasma of a human having a normal endogenous melatonin plasma profile.

In another aspect, the invention provides a pharmaceutical controlled-release formulation, which comprises melatonin in combination with at least one pharmaceutical carrier, diluent or coating, the Formulation being adapted to release melatonin Following administration to a human patient, over a predetermined time period, in an amount such that melatonin release occurs according to a profile which, taking into account the existing profile, simulates the profile in plasma of a human having a normal endogenous melatonin profile.

BRIEF DESCRIPTION OF THE DRAWINGS

FIG. 1 illustrates the nocturnal profile of melatonin concentration in a healthy adult human, which exemplifies the profile to be simulated in accordance with the present invention.

DETAILED DESCRIPTION OF THE INVENTION

The formulation in accordance with the invention may be formulated for a mode of administration selected from oral, parenteral, rectal and transdermal administration, and may contain, e.g., 1 ng–80 mg melatonin per dosage unit.

In a presently preferred embodiment of the formulation according to the invention, the melatonin is in particulate form comprising coated particles and the desired release profile is achieved by at least one of the following characteristics, namely:

(a) by variation in the particle size of the melatonin;

(b) by use of at least two different coating materials which dissolve at different rates in the human body; and (c) by varying the thickness of coating material(s) whereby particulate melatonin coated with different thicknesses of coating material(s) dissolve at different rates in the human body.

In such an embodiment of the invention, the formulation may e.g. comprise particulate melatonin coated with at least one polymeric coating material, e.g. selected from natural and synthetic polymer coating materials.

The Formulation of the invention may be administered e.g. once or twice daily at preselected times, in order to achieve the desired simulation of the plasma melatonin profile. Preferably, the formulation will be administered before sleep, so that the desired profile will be achieved while the patient sleeps.

Persons skilled in the pharmaceutical art will be able to formulate the controlled-release formulations of the present invention on the basis of the information given in the present specification, in conjunction with the knowledge of persons skilled in the art in relation to known slow release or controlled-release formulations.

Administration of melatonin in accordance with the present invention includes the co-adminstration therewith of one or more substances which alter the phase position or shape of melatonin receptor profiles. A non-limiting example of such melatonin receptor profile modifiers is oxazepam, which may potentiate the response to melatonin by affecting the phase position of the receptors. In accordance with an embodiment of the invention at, least one such modifier, e.g. oxazepam, may be included in the pharmaceutical formulation of the invention.

It will be appreciated that the present invention may serve to correct abnormalities in the timing, duration or slope, in any particular part of the human nocturnal plasma melatonin level. FIG. 1, which is based on a publication of McIntyre et al in J. Pineal Research, 4:177–183 (1987), is an example only of a normal human plasma profile, which is simulated in accordance with the present invention. The simulation of other human plasma melatonin profiles, which may differ from that of FIG. 1 because of e.g., the age or sex of the patient, or the season of the year, is of course within the scope of the present invention.

The experiments which Follow are believed to constitute indications of the potential utility of the present invention.

IN VIVO EXPERIMENTS

Experiment

The distribution of melatonin binding sites in five discrete brain areas of sham-operated (where the same intracranial surgery has been performed but the pineal gland though touched with forceps was not removed) and pinealectomized young male rats was investigated, at intervals of 5, 13 and 19 hours after lights-on, in a 14 hour light/10 hour dark cycle, 18 days after surgery, using $^{125}$I-melatonin as a probe. In the pinealectomized rats, the densities of $^{125}$I-melatonin binding sites in the hypothalamus, hippocampus and medulla-pons, exhibited clear diurnal variations, which resembled in amplitude those in the corresponding brain areas of the sham-operated rats; the densities of binding sites in these brain areas were higher in the sham-operated, but lower in the pinealectomized animals, at 13 hours after lights-on than at other times of the day tested. The data suggested that the pineal gland mediates the coupling of the rhythm in melatonin receptors to the circadian clock, whereas the rhythm in melatonin receptors runs freely in absence of the pineal gland at a period of about 23.5 h; the phase advance of about 8 hours (ca. 0.5 h per day) may thus represent the time by which the acrophase has 'drifted' from the external light-dark cycle during the 18 days after surgery.

Experiment 2

The impact of exogenously administered melatonin on central melatonin binding sites and serum testosterone in aged male rats was investigated. Thus, 23-month old male rats were treated with melatonin via the drinking water for 30 days. This melatonin supplementation in the aged Fat markedly increased melatonin binding sites in the hypothalamus, medulla-pons, thalamus and cortex, and attenuated a suppressive effect of testosterone on melatonin binding sites in steroid-dependent areas (hypothalamus and hippocampus). Serum testosterone levels in the melatonin treated animals did not significantly differ from the values in untreated controls.

Experiment 3

The effects on 8–10 month old adult Fats, of long term (~18 months) administration of melatonin via the drinking water (4 mg./l), on the survival, on central melatonin binding sites, and on serum testosterone, were investigated. Melatonin supplementation markedly increased the number of rats surviving at the age of 24–29 months. In more detail, only 8 of a control group of 16 animals survived at age 26–28 months, and 7 at age 27–29 months, whereas 13 of a melatonin-treated group of 15 animals survived at age 26–28 months and these continued to live at age 27–29 months, when the experiment was terminated by sacrifice of the animals. The significance of the difference in survival was P=0.01 according to two by two Pearson's Chi square test. In addition, the melatonin-treated animals either did not suffer from pneumonia, or had only very weak symptoms; in the control group, 5 of the 7 survivors had severe pneumonia. Melatonin supplementation significantly increased melatonin binding sites in the medulla-pons and hypothalamus in aged rats, and the circadian variations in melatonin binding areas were still evident despite the old age of the animals. Serum testosterone levels in the melatonin treated animals was significantly higher than the values in the untreated controls.

The results of Experiments 2 and 3 demonstrate the advantages of long term melatonin treatment beginning prior to the derangement of the circadian system in the aged, compared with merely short-term treatment in the aged.

Experiment 4

The effects of daily injections over a 14-day period, of the short-term acting benzodiazepine oxazepam, on melatonin binding sites in the rat brain, in both presence and absence of the pineal gland, were investigated. In sham-operated rats specific binding of $^{125}$I-melatonin in all brain areas investigated, exhibited clear diurnal variations. However, the densities of binding sites in these brain areas were higher at midnight (i.e. 19 h after lights-on) in the oxazepan-treated, against the peak at 13 hours after lights-on recorded in the untreated rats. In the pinealectomized rats, melatonin binding in the hypothalamus, hippocampus and medulla-ports, also exhibited clear diurnal variations but phase-shifted as compared to intact or sham operated controls; the densities of binding sites in these brain areas were lower at 13 hours after lights-on than at other times of the day. Daily oxazepam injections decreased melatonin binding sites at 19 hours after lights-on but did not significantly effect the binding at other times of the day.

Melatonin administration via the drinking water had no effect on $^{125}$I-melatonin binding in the various brain areas of the pinealectomized rats at any of the times recorded. In the sham-operated rats, melatonin administration led to a decrease in $^{125}$I-melatonin binding recorded at 13 hours after lights-on in the hippocampus and midbrain.

These results indicate that (a) the diurnal variations in $^{125}$I-melatonin binding sites in the rat brain are not generated by the pineal gland; (b) oxazepam modifies the diurnal variations in $^{125}$I-melatonin binding sites in the rat brain in the presence of the pineal gland and is less effective in its absence; (c) in the absence of the pineal gland, the diurnal rhythms of melatonin binding sites in the rat brain are not synchronized with the circadian clock; (d) supplementation of melatonin to pinealectomized rats via the drinking water does not reverse the phase advance of the rhythm in $^{125}$I-melatonin binding.

Discussion

The failure of melatonin supplementation to phase shift the melanin binding sites rhythms in the brain of pinealectomized rats may be related to the time and mode of its administration. Indeed, simulation of nocturnal pineal melatonin release by injections of melatonin at the time of endogenous melatonin production (2 hours prior to the end of the dark phase) has been shown to restore sensitivity to late afternoon melatonin injections in pinealectomized hamsters, but the injections were ineffective at any other time of day (Watson-Whytmyre and Stetson, Endocrinology, 112:763 (1983).

Hence, the exact timing and profile of the melatonin peak may be crucial to achieve entrainment of melatonin binding site rhythm. This problem is even more crucial in humans. Being nocturnal, the rat is especially active at the beginning and end of the dark period, during which it also drinks. Consequently, orally administered melatonin in the rat may be ingested predominantly during the night, like endogenous melatonin. In contrast, in the human, simulation of melatonin peak by conventional oral ingestion may be difficult to achieve since man is a diurnal species and the peak production of melatonin around 2 a.m. occurs during sleep. Thus, to compensate for the obliteration of the nocturnal rise in melatonin and to correct distortions in the shape and phase position of the melatonin peak in humans, it is proposed in accordance with the present invention, to administer melatonin via a slow release composition, designed to fit various shapes and patterns such as those present in children or in adults, at various seasons of the year.

Experiment 5

The circulating melatonin was measured in a hospital medical crew of seven who worked during the night in an illuminated room. It was found that 2/7 had no significant melatonin rhythm at all and 3/7 had impaired rhythms. Such cases would seem to be suitable subjects for the application of the present invention.

APPLICATIONS OF THE INVENTION

The function and usefulness of melatonin in the human or animal body is a complex subject about which many scientific papers and a number of patents have been published within the last few years. Yet to the best of the inventor's knowledge, notwithstanding the intensive research and numerous publications on this subject, the particular method and formulation for the treatment of melatonin-deficiency or distortion related conditions has not been proposed hitherto. It is believed that the present invention will make possible the improved treatment of melatonin-deficiency or distortion related conditions.

Without detracting from the generality of the potential applications of the present invention, it may be noted that sudden infant death syndrome (SIDS) or cot death is a phenomenon in which an apparently healthy infant of 1–12 months of age dies suddenly, usually during sleep. It has been shown that while body and brain weight of age-matched control and SIDS infants were not significantly different, the size of the pineal gland was significantly reduced in SIDS infants (p<0.000; Sparks and Hunsakep, J.

Pin. Res. 5:111 (1988), and Abstract No. 127 of the 5th Colloquium of the European Pineal Study Group, Guildford, U.K., Sep. 2, 1990). Additionally, melatonin levels in the SIDS infant blood were lower by about 50% in SIDS compared with control infants (p<0.05; Wuztman and Lynch, Abstract No. 24 of the 5th Colloquium of the European Pincal Study Group, Guildford, U.K., Sep. 2, 1990) as seems likely from these reports, melatonin serves a critical role in sleep functions of the human infant, simulation of melatonin signal by the method or by use of the controlled-release formulations in accordance with the present invention could prevent SIDS in infants.

Accordingly, the present invention further provides a method for the prevention of sudden infant death syndrome in infants, which comprises the steps of: (a) screening infants in order to determine their plasma melatonin levels; (b) selecting infants shown in step (a) to have deficient plasma melatonin levels; and (c) administering to this selected infants from step (b) over a predetermined time period, an amount of melatonin in controlled-release form, such that the melatonin is released according to a profile which, taking into account the existing profile, simulates the profile in plasma of an infant of comparable age having a normal endogenous melatonin plasma profile.

It will be appreciated that infants treated in accordance with the invention can be monitored in order to determine when it is safe to discontinue such administration which thus simulates the normal melatonin plasma profile.

Other indications which may be amenable to treatment in accordance with the present invention include, by way of example, treatment of infertility, cause unknown, but possibly due to inappropriate timing of the melatonin peak; affective disorders and migraine which are associated with phase advances in the melatonin peak; and impaired seasonal adaptation due to improper duration or shape of the melatonin peak.

While particular embodiments of the invention have been particularly described hereinabove, it will be appreciated that the present invention is not limited thereto, since, as will be readily apparent to skilled persons, many variations and modifications can be made. Such variations and modifications which have not been detailed herein are deemed to be the obvious equivalents of the present invention. For example, analogs of melatonin which substantially imitate the Function of melatonin in the human body are deemed to be obvious chemical equivalents of melatonin. The essential concept, spirit and scope of the present invention will be better understood in the light of the claims which follow.

I claim:

1. A pharmaceutical controlled-release formulation in dosage form which consists essentially of melatonin in combination with at least one pharmaceutical carrier, diluent or polymeric coating, which formulation contains 1 ng to 80 mg melatonin per dosage unit and releases melatonin in the plasma following administration to a human patient according to a profile which simulates that of the endogenous melatonin profile depicted in FIG. 1 herein.

2. A formulation according to claim 1, which is formulated for a mode of administration selected from oral, parenteral, rectal and transdermal administration.

3. A formulation according to claim 1, wherein the melatonin is in particulate form comprising polymer-coated particles and the desired release profile is achieved by at least one technique selected from the group consisting of:

(a) variation in the particle size of the melatonin;

(b) use of at least two different polymeric coating materials which dissolve at different rates in the human body; and (c) varying the thickness of polymeric coating material(s) whereby particulate melatonin coated with different thicknesses of coating material(s) dissolve at different rates in the human body.

4. A formulation according to claim 1, which comprises particulate melatonin coated with at least one polymeric coating material.

5. A pharmaceutical controlled-release formulation in unit dosage form which consists essentially of melatonin and oxazepam as a melatonin receptor profile modifier in combination with at least one pharmaceutical carrier, diluent or polymeric coating, which formulation contains 1 ng to 80 mg melatonin per dosage unit and releases melatonin into the plasma following administration to a human patient according to a profile which simulates that of the endogenous melatonin profile depicted in FIG. 1 herein.

6. A method for treating a patient having at least one condition selected from the group consisting of a melatonin deficiency and a distortion in the plasma melatonin endogenous profile which comprises administering to the patient, over a predetermined time period including at least part of the nocturnal period between 9:30 p.m. and 8:00 a.m., an effective plasma melatonin deficiency or endogenous plasma melatonin profile distortion correcting amount of melatonin in the form of a pharmaceutical controlled-release formulation in unit dosage form which consists essentially of melatonin in combination with at least one pharmaceutical carrier, diluent or polymeric coating, which formulation contains 1 ng to 80 mg melatonin per dosage unit and releases melatonin into the plasma following administration to a human patient according to a profile which simulates that of the endogenous melatonin profile depicted in FIG. 1 herein.

7. A method according to claim 6, wherein said formulation is formulated for a mode of administration selected from oral, parenteral, rectal and transdermal administration.

8. A method according to claim 6, wherein the melatonin is in particulate form comprising coated particles and the desired release profile is achieved by at least one technique selected from the group consisting of:

(a) variation in the particle size of the melatonin;

(b) use of at least two different polymeric coating materials which dissolve at different rates in the human body; and (c) varying the thickness of polymeric coating material(s) whereby particulate melatonin coated with different thicknesses of coating material(s) dissolve at different rates in the human body.

9. A method according to claim 6, wherein the melatonin is in the form of particulate melatonin coated with at least one polymeric coating material.

10. A method for treating a patient having at least one condition selected from the group consisting of a melatonin deficiency and a distortion in the plasma melatonin endogenous profile, which comprises:

administering to the patient, over a predetermined time period including at least part of the nocturnal period between 9:30 p.m. and 8:00 a.m., an effective plasma melatonin deficiency or endogenous plasma melatonin profile distortion-correcting amount of melatonin in the form of a pharmaceutical controlled release formulation in unit dosage form, wherein the formulation consists essentially of melatonin and oxazepam with at least one pharmaceutical carrier, diluent or polymeric coating, which formulation contains 1 ng to 80 mg melatonin per dosage unit and releases melatonin into the plasma following administration to the patient such that the patient's plasma melatonin profile simulates that of the endogenous melatonin profile depicted in FIG. 1 herein.

* * * * *

UNITED STATES PATENT AND TRADEMARK OFFICE
CERTIFICATE OF CORRECTION

PATENT NO. : 5,498,423
DATED : March 12, 1996
INVENTOR(S) : Nava Zisapel

It is certified that error appears in the above-indentified patent and that said Letters Patent is hereby corrected as shown below:

Title page, Item [73] Assignee, before "Israel", insert -- Tel Aviv, --; Col. 2, line 41, "Over" should be -- over --; Col. 2, line 55, the period in the middle of the sentence should be a comma; Col. 3, line 23, "Formulation" should be -- formulation --; Col. 3, line 24, "Following" should be -- following --; Col. 3, line 62, "Formulation" should be -- formulation --; Col. 4, line 28, "Follow" should be -- follow --; Col. 4, line 33, after the subheading "Experiment", insert -- 1 --; Col. 4, line 63, "Fat" should be -- rat --; Col. 5, line 7, "Fats" should be -- rats --; Col. 6, line 67, "Hunsakep" should be -- Hunsaker --; Col. 7, line 8, after "1990)" insert -- . If, --; Col. 7, line 42, "Function" should be -- function --.

Signed and Sealed this

Twentieth Day of August, 1996

Attest:

BRUCE LEHMAN

*Attesting Officer*  *Commissioner of Patents and Trademarks*